United States Patent
Gao

[11] Patent Number: 5,606,984
[45] Date of Patent: Mar. 4, 1997

[54] AUTOMATIC DENTAL FLOSSING DEVICE

[76] Inventor: Yong Gao, 981 Gulf Place, Apt. 714, Ottawa, Ontario, Canada, K1K 3X9

[21] Appl. No.: 351,345
[22] PCT Filed: Sep. 30, 1992
[86] PCT No.: PCT/CA92/00415
    § 371 Date: Dec. 8, 1994
    § 102(e) Date: Dec. 8, 1994
[87] PCT Pub. No.: WO94/00075
    PCT Pub. Date: Jan. 6, 1994

[30] Foreign Application Priority Data
Jun. 26, 1992 [CA] Canada ................... 2072555

[51] Int. Cl.⁶ ................................. A61C 15/00
[52] U.S. Cl. ............... 132/325; 132/322; 132/323; 132/327; 132/328
[58] Field of Search ................... 132/325, 322, 132/323, 327, 328

[56] References Cited

U.S. PATENT DOCUMENTS

| | | | |
|---|---|---|---|
| 3,667,483 | 6/1972 | McCabe | 132/322 |
| 3,759,274 | 9/1973 | Warner | 132/322 |
| 4,245,658 | 1/1981 | Lecouturier | 132/322 |
| 4,586,521 | 5/1986 | Urso | 132/322 |
| 5,269,331 | 12/1993 | Tanriverdi | 132/325 |
| 5,323,796 | 6/1994 | Urso | 132/322 |

Primary Examiner—Nicholas D. Lucchesi
Assistant Examiner—Pedro Philogene

[57] ABSTRACT

A power-driven dental flossing device has an elongate housing of three casings with an extending housing arm forked at its front, which contains dental floss reels, a dividing gear system, dental floss operating and winding switches, and a powered motor with batteries and/or a transformer. Dental floss across two tines of the forked arm is wound on the two reels, one of which supplies fresh dental floss, the other takes up used floss. The dental floss can be automatically reciprocated between the tines and teeth by pulling an operating switch backward, and also can be manipulated manually by pushing the same operating switch forward. The floss can also be automatically wound in one direction at time to provide a fresh length of the floss, or to rewind it back at any time. The floss reels are driven by the gear system which comprises pinions installed on reel shafts, and a main dividing gear with partially geared circumference to drive each one of pinions alternately, therefore the dental floss can automatically complete reciprocating motion to accomplish teeth cleaning. The main gear can also be slid to an upper or lower position on its shaft where only one pinion could be driven by the main gear, therefore the dental floss will be continually wound only in one direction at a time.

8 Claims, 7 Drawing Sheets

Fig.9
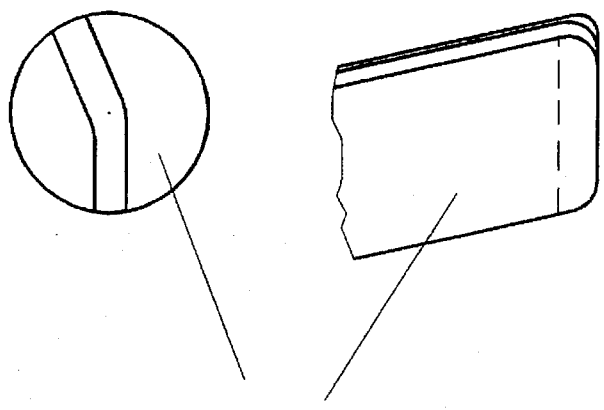
Fig.10
24
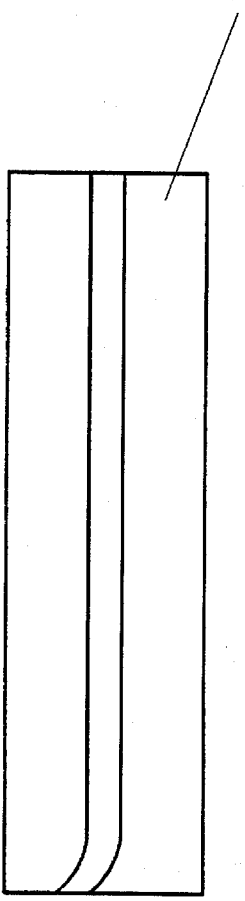
Fig.8

AUTOMATIC DENTAL FLOSSING DEVICE

SUMMARY OF THE PRESENT INVENTION

The principal object of the present invention is to provide an effective, easy-to-use and power-driven device for optimizing and comforting the process of using a dental floss to clean teeth.

In accordance with this invention, there is provided an automatic dental flossing device comprising an elongate housing handle with an extending thinner arm forked at its front end, in which a pair of removable reels with dental floss on them, a transmission gear system, an operating switch, a winding switch and a powered motor are installed. The handle is divided into three casings which are the upper, bottom and rear casings, respectively. The upper casing is openable for storing or changing the dental floss on the two reels. The gear system is mounted in the bottom casing. The motor is in the rear casing.

A pair of guiding slots are grooved on the forked arm which has a pair of slotted conducting tube-like means on its two tines, for guiding the dental floss from the upper casing to the tines of the forked arm.

The dental floss, stretched across the two tines of the forked arm, is guided into the handle and wound on the two reels one of which supplies fresh dental floss, another of which takes up the used one.

The dental floss can be automatically reciprocated by pulling the operating switch means backward, or tightly held by pushing the same switch means forward. Tension of the dental floss is controllable. On the other hand, the dental floss can be wound continually in one direction, backward or forward, by using the winding switch means.

The pair of removable reels carrying the dental floss are driven by the transmission gear system which comprises a primary gear with partially geared circumference, a belt, and two pinions installed on two separate shafts on which the two reels are also installed.

The primary gear can be moved into three engaging positions to alternately drive the two pinions, or engage only one of them, so the dental floss will be manipulated in three different operating modes for reciprocating, supplying or rewinding the dental floss.

The driving belt deliver power from the motor to the primary gear, having flexibility of slipping on the shafts to release any unexpected overload for protecting the device and user as well.

BRIEF DESCRIPTION OF THE DRAWINGS

Referring particularly to the drawings for the purpose of illustration only and not limitation, there is illustrated:

FIG. 8 is an enlarged side plane view of the slotted conducting tube-like means installed onto two tines of the arm of the said device;

FIG. 9 is an enlarged front elevational view of the tube-like means;

FIG. 10 is a local cross section vertical view of the tube-like means in a tine of the forked arm;

DETAILED DESCRIPTION OF THE INVENTION

Figure 1:
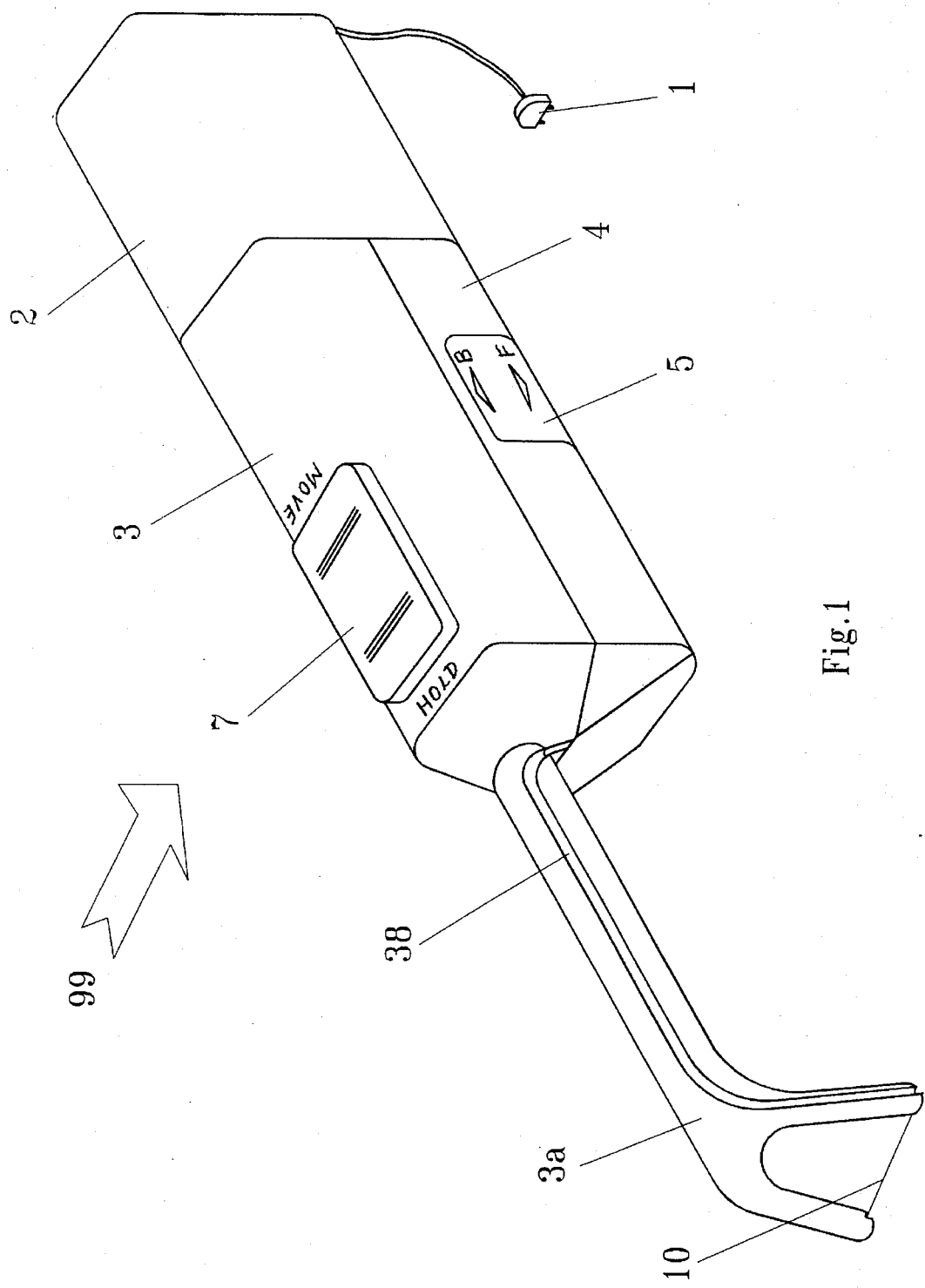
FIG. 1 is a side perspective view of a dental flossing device constructed pursuant to the present invention.
Figure 2:
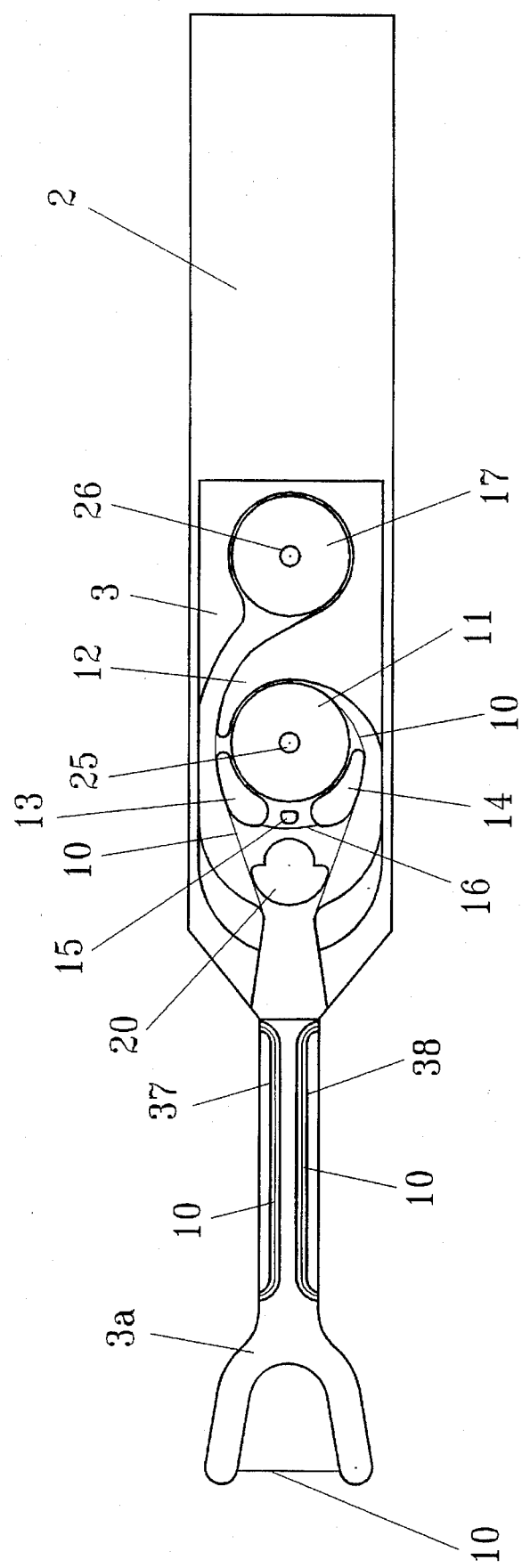
FIG. 2 is a vertical view of said device, partially uncovered, showing general lay-out and positions of the dental floss, the two reels and a part of the operating switch.
Figure 3:
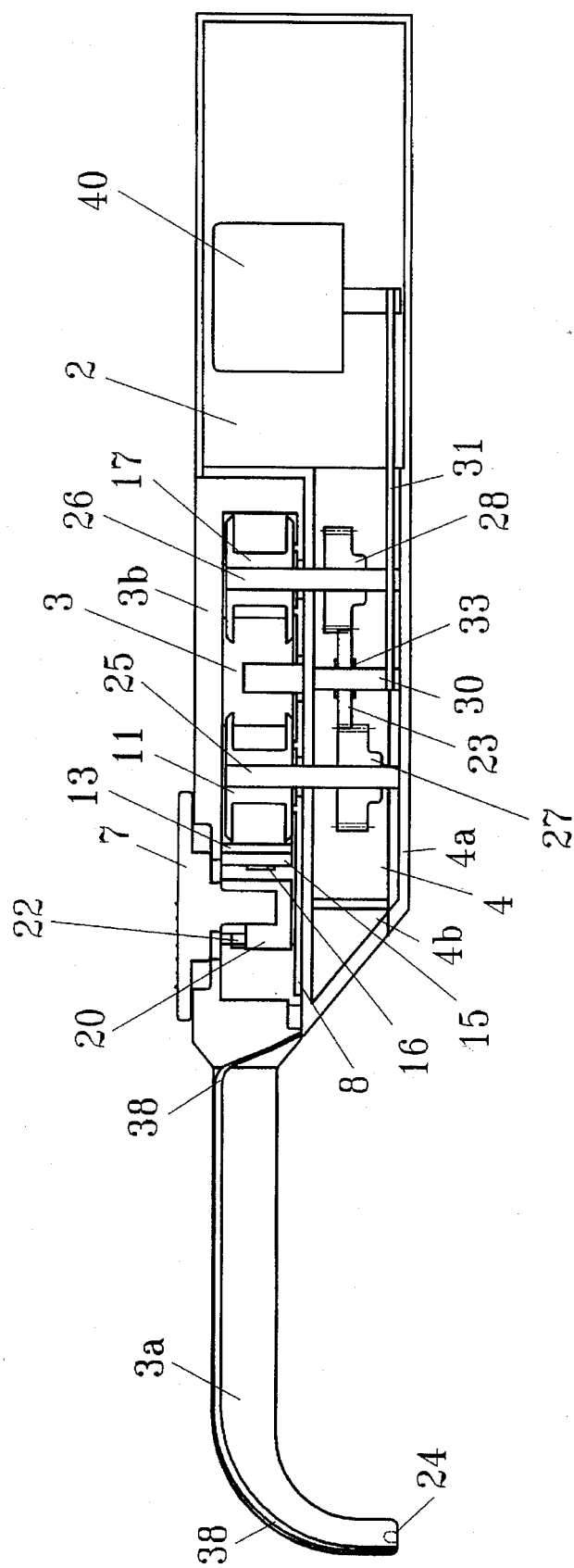
FIG. 3 is a longitudinal cross-section view of the said device, mainly illustrating lay-out of the transmission gear system, two reels and the operating switch.
Figure 5:
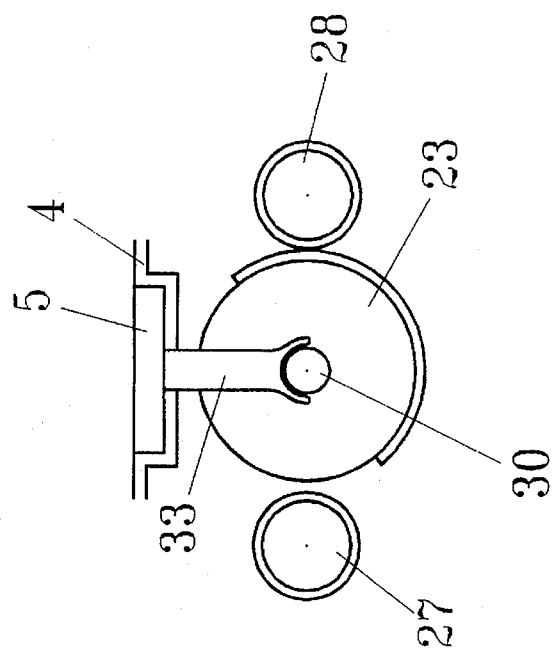
FIG. 5 is a right side view of FIG. 4, schematically illustrating the shape of the winding switch yoke.
Figure 4:
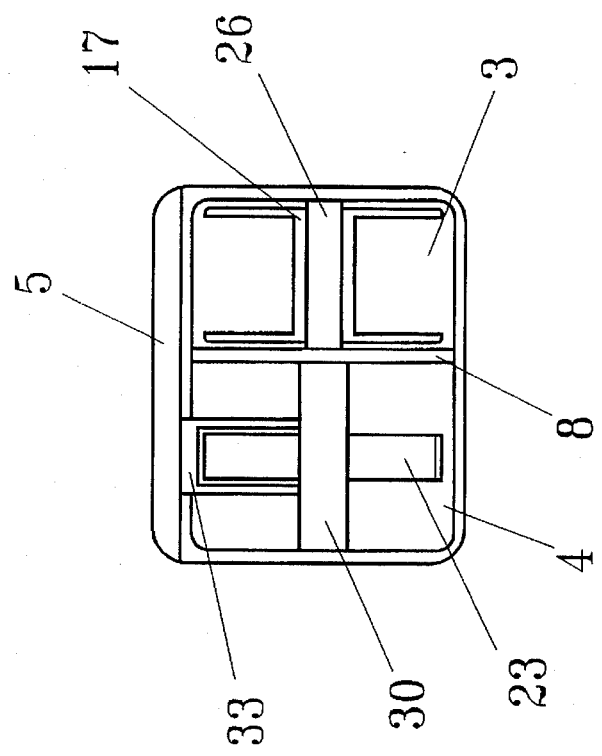
FIG. 4 is a cross-section side view of the handle, showing the winding switch with a yoke for moving the primary gear up and down.
Figure 7:
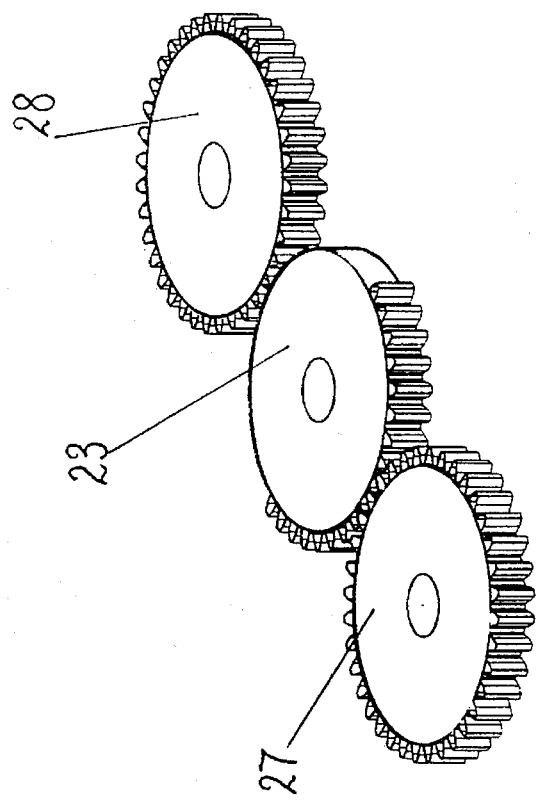
FIG. 7 is a perspective view of lay-out of the three gears.

The present invention relates generally to an oral hygiene system, specifically concerning a device suited to support and operate a dental floss. There have been some known inventions which allow improvements in the use of the dental floss by trying to make such use easier and more efficient, such as the European patent application No. 0 453 418 A1, which has both new and used dental floss virtually starting and ending on a reel and a tube mounted on a concentric shaft driven by a complicated gear system, and continuously consumes the floss during the operation without user's instruction of replacing it, the U.S. Pat. No. 3,759,274, which has a dually (outer and inner) geared ring with partial teeth on its inner circumference and both new and used floss wound on a spool driven by a concentric tapered gear, without flexible means to firmly hold a floss for the manipulation of the floss, U.S. Pat. No. 4,245,658, having a more complicated mechanism, U.S. Pat. No. 3,847,167, which has a camrod driving system to operate a dental floss ring, U.S. Pat. No. 3,667,483, having a cam-like operating system, and U.S. Pat. Nos. 5,060,681, 5,020,554, 4,830,032, 5,038,806 and 4,920,992, the German patent application No. DE 3625991 and 3635608, and Canadian patent 1266193. All of these inventions claim devices of operating a dental floss, with various features some of which are similar, such as supporting a dental floss stretched between two tines of a fork for the purpose of cleaning teeth. Although the present invention and the prior art floss applicators share some similar features, it is believed that a number of features of the present invention are patentably distinct over all the prior art disclosures. Inclusive of such distinctive features, although not limited thereto, are the simple and easy constructed motion mechanisms, the one-touch, floss reciprocating or holding/locking arrangement, the free and easy floss advancing and rewinding capability, and both one way running and reciprocating the floss for cleaning teeth, and so on.

Although specific embodiments of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Referring descriptively to the drawings, a power-driven fully automatic dental flossing device 99 is configured in an elongate housing handle with an extending thinner arm forked at its front end, and/or with the plug-in transformer 1 connected on.

The handle is constructed with three casings which are an upper casing 3 formed with an attached elongate arm 3a forked at its front, a frame 3b and a bottom section 8; a bottom casing 4 formed with a frame 4b and a bottom cover 4a; and a rear casing 2 openable for installing a power system including the motor 40 and related accessories.

The upper casing 3, having guiding paths formed with the contoured guiding knobs 12, 13 and 14, and the contoured inner wall of the casing frame for guiding the dental floss 10, is openable and replaceable through either screwing or snap-fitting means of known types or any other fixing means, for the purpose of installing and replacing the dental floss 10, and contains a pair of reels 11, 17 installed on the shafts 25, 26 separately, and an operating switch means.

A pair of guiding slots 37, 38 are grooved on the forked arm 3b of the upper casing 3 for handling the dental floss 10 from inside of the upper casing 3 to its forked arm tines.

The bottom casing contains two separate reel shafts 25 and 26 extended into the upper casing 3 for driving the reels 11, 17, respectively, a winding switch means, and a transmission gear system comprising a primary gear 23 slidable on a primary gear shaft 30, a driving belt 31 and two pinions 27, 28 installed on the shafts 25, 26.

The openable rear casing contains a powered motor 40 which delivers power through the belt 31, other related accessories of known types for the purpose of controlling and operating the motor 40, batteries, and/or a plug-in transformer 1.

The dental floss 10 stretched between the two tines of the forked arm 3a, through the pair of guiding slots 37 and 38 on the arm, is wound on the two reels 11 and 17 one of which supplies fresh dental floss and another of which takes up the used floss. Which reel is used for fresh floss is user's choice.

Figure 6:
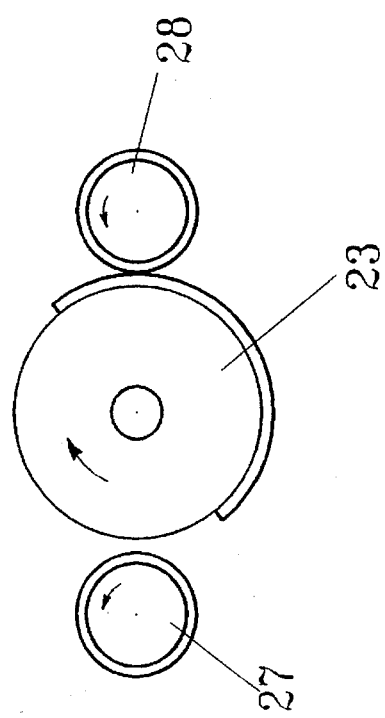
FIG. 6 is a schematic to indicate the connection and rotating direction of the three gears.

The pair of removable reels 11 and 17 carrying the dental floss 10 are driven by the transmission gear system. When engaged in a middle position, the primary gear 23 of the system, having only partially geared circumference (as an exemplary arrangement shown in the attached drawings, 180° circumference of the primary gear has gear teeth), alternately drives the two adjacent pinions 27 and 28. For every full rotating cycle of the primary gear, each one of the two pinions is driven a half of the cycle. Accordingly, the reels 11 and 17 will be in turn either a driving reel to wind the dental floss 10 onto itself or a following reel to release the dental floss off itself. A further explanation of this mechanism can be expressed as follows: once the primary gear 23 runs clockwise, both pinions 27 and 28 along with the two reels 11, 17, will be driven counter clockwise correspondingly as shown in FIG. 6; and because the guiding paths in the upper casing 7 introduce the dental floss 10 into the same side of the rear reel 17 as of the front reel 11, both of the reels 11 and 17 will be always winding the dental floss 10 back, once alternately engaged on the primary gear 23. In one word, because each one of full rotating cycles of the primary gear 23 is divided into two half cycles by its partially geared circumference to drive the reels 11,17 through the two pinions 27, 28, for alternately winding the dental floss 10 back, the reciprocation of the dental floss 10 stretched between the two tines of the arm 3b is formed to accomplish teeth cleaning.

The operating switch means in the upper casing 3 comprises the switch button 7, the contoured switch frame 20, a spring 22, a knob 15 as an electrical pole of the operating circuit, and a spring 16 as another pole bridged between the two guiding knobs 13, 14. Once the operating switch means is pulled backward to the MOVE position (see FIG. 1) where the spring 16 is pressed to touch the knob 15, the motor 40 will be turned on to provide power for the device 99. Or the dental floss can be tightly held from any motion by pushing the switch means forward to the HOLD position where the contoured switch frame 20 presses the dental floss against the matching-contoured inner wall of the upper casing 3. The operating switch means will be moved back to a middle neutral position by the springs 16 or 22 from either the MOVE position or HOLD position as soon as the switch button 7 is released.

The winding switch means installed on the frame 4b of the bottom casing 4, comprises a switch button 5 and a yoke-like frame 33 riding across the primary gear 23. The winding switch means can set up the gear 23 into three engaging positions: the above mentioned middle position for reciprocating the dental floss 10, an upper position and lower position for the purpose of supplying fresh floss or rewinding the floss back, even while the dental floss 10 is still in between teeth, and the user only needs temporarily to release the operating switch means and manipulate the winding switch means.

Once the primary gear 23 is moved up and down into the above mentioned upper or lower position, only one of the pinions can be engaged on the primary gear 23. Therefore, the dental floss 10 will be continually wound only in one direction, either forward or backward, and the above mentioned functions of supplying and rewinding the dental floss 10 can also be automatically accomplished.

If a user prefers using a section of the floss 10 between his/her teeth only once for the purpose of better hygienic cleaning, the said winding switch means is also able to provide the advantage and flexibility of one way running the floss to accomplish teeth cleaning, by continually supplying the dental floss forward.

The driving belt 31, delivering power from the motor 40 to the primary gear 23, is able to slip on either the motor shaft or the primary shaft 30 for releasing any unexpected overloading force on the gears, for instance, the dental floss 10 may be stuck between user's teeth incidently. Therefore, the device 99 can be prevented from any unexpected damage, the dental floss 10 will not be broken down and the user will not be hurt.

Figure 11:
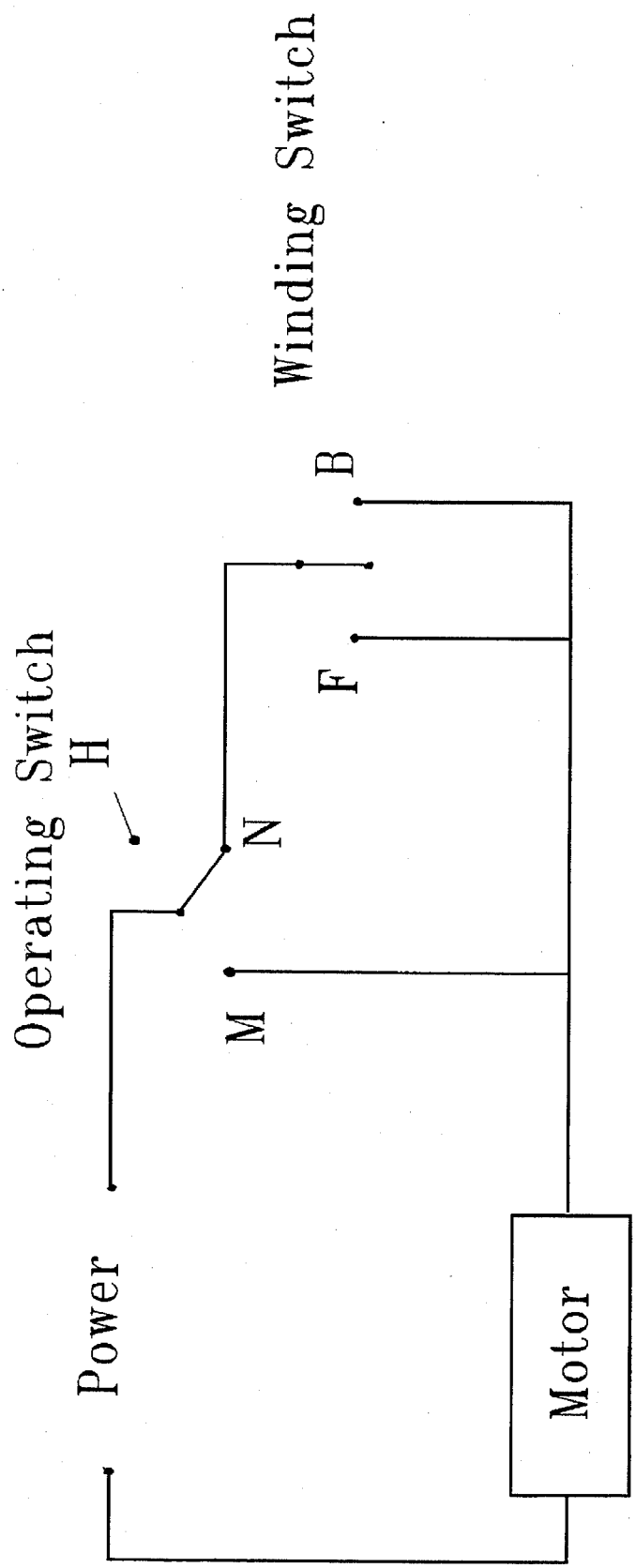
FIG. 11 is a schematic of electric circuit, showing connection of the two switches.

The operating switch means and the winding switch means are arranged in a circuit in order of priority as shown in FIG. 11. Once the switch button 7 is at point M representing the MOVE position or at point H for the HOLD position, the electric connection of the winding switch means is automatically cut off, although it is still movable to point F or point B. Therefore the said device 99 is well protected against any electric damage.

An exemplary apparatus usable with the present invention may be the transformer 1 which may take safe voltage ranging from 120 volts to 240 volts at a rated frequency of 50 to 60 Hz and provide a secondary voltage ranging from 14 volts per 50 Hz or 14 volts per 60 Hz. The transformer may have an output power of about 3 watts, designed for continuous operation in idle running and is connected to the motor 40.

What is claimed is:

1. A power-driven fully automatic dental flossing device, wherein a dental floss is automatically reciprocated or continually run in one direction, and said device comprising:

(a) housing means containing an apparatus for automatically manipulating the dental floss, and formed with a frame comprising an openable and replaceable upper casing, a bottom casing, and a rear casing, and two tines attached to a forked arm extending from the upper casing;

(b) guide means formed on said upper casing for guiding the dental floss through a proper path to accomplish desired functions;

(c) reel means mounted in said upper casing of said housing means for supplying fresh dental floss and taking up used floss, for winding the dental floss in one direction at a time, and for reciprocating the floss back and forth;

(d) transmission means installed in the bottom casing for transmitting power and driving said reel means to accomplish automatic manipulation of the dental floss;

(e) operating switch means for switching on and off said device to reciprocate the dental floss, and for holding said dental floss;

(f) winding switch means for switching on and off said device to continually wind the dental floss in one direction at a time back and forth;

(g) power means installed in said rear casing to provide power for automatically manipulating the dental floss; and (h) slotted tube conducting means on said tines of said forked arm for conducting the dental floss across said tines and integrating tips of said tines against cracking and wearing.

2. The invention in accordance with claim 1, wherein said upper casing of said housing means can be openable and replaceable for installing and replacing said reel means.

3. The invention in accordance with claim 1, wherein said guide means comprises a group of contoured guiding knobs, grooved slots on said forked arm, and a contoured inner wall of said frame of said upper casing for accommodating and guiding the dental floss from said reel means to the tines of said forked arm of said upper casing.

4. The invention in accordance with claim 1, wherein said reel means comprises a set of removable reels, carrying a dental floss and accommodated on separate shaft mechanisms of said transmission means, one of which supplies fresh dental floss, and another of which takes up used dental floss, and is able to reciprocate the dental floss between teeth and supply a fresh length of the dental floss at any time even while the dental floss is still in between the teeth.

5. The invention in accordance with claim 1, wherein said transmission means comprises a set of driving belts with flexible mounting force for preventing said device from any overloads, a set of separated shaft mechanisms extended into said upper casing for driving said reel means and a set of gears including speed-adjusting gears, and a primary gear slidable on its shaft driven by said power means through said belts and having partially geared circumference for dividing its every whole cyclic rotation into several sections to drive following gears, either alternately in the case where more than one of said gears are engaged, or continually in the case where a single gear is engaged, according to the different positions engaged by said slidable primary gear.

6. The invention in accordance with claim 1, wherein said operating switch means, comprising an operating button, a contoured frame, springs and knobs, said switch means adapted to press the dental floss against inner walls of said upper casing of said device for holding the dental floss tightly, and to switch on/off said device for automatically reciprocating the dental floss which tension is controllable.

7. The invention in accordance with claim 1, wherein said winding switch means comprises a manipulating mechanism to move said primary gear up or down into three different positions with a middle position allowing said primary gear to alternately drive all the engaged following gears, and upper and lower positions allowing for said primary gear to engage only one of said following gears and simultaneously switch on said device for continually winding the dental floss in one direction at a time.

8. The invention in accordance with claim 1, wherein said slotted tube means is coupled to fit onto each one of said two tines of said forked arm, having slots positioned at outside higher sections of said tines of said forked arm, for conducting the dental floss smoothly across the tips of said tines and integrating said tines of said arm against cracking and wearing.

* * * * *